United States Patent [19]

Hughes

[11] 4,284,406
[45] Aug. 18, 1981

[54] DENTAL TOOTH BUR

[76] Inventor: Thomas E. Hughes, 6024 Fallbrook, Suite 103, Woodland Hills, Calif. 91367

[21] Appl. No.: 179,298

[22] Filed: Aug. 19, 1980

[51] Int. Cl.³ .............................................. A61C 3/00
[52] U.S. Cl. .................................... 433/165; 407/53; 407/61
[58] Field of Search .................... 433/165; 407/34, 42, 407/53, 54, 61, 62, 63

[56] References Cited

U.S. PATENT DOCUMENTS

| 418,108 | 5/1889 | Browne | 433/165 |
|---|---|---|---|
| 683,696 | 10/1901 | Maillard | 433/144 |
| 846,666 | 3/1907 | Hanson | 408/229 |
| 1,409,921 | 11/1922 | Buck | 408/229 |
| 1,478,414 | 12/1923 | Wells | 408/224 |
| 1,813,741 | 7/1931 | Harper | 433/165 |
| 1,827,511 | 10/1931 | Evans | 433/165 |
| 2,898,612 | 8/1959 | Hofbrauer | 408/216 |

OTHER PUBLICATIONS

"S. S. White Burs", 2 pp., Feb. 1975, Dental Products Div., Phila., PA 19102

Primary Examiner—Robert Peshock
Attorney, Agent, or Firm—Poms, Smith, Lande & Rose

[57] ABSTRACT

A dental tooth bur includes a plurality of flutes longitudinally disposed at one end of a shank and adapted to produce a prepared cavity having a wall that has a plurality of generally microretentive ridges in its lower portion and that is generally smooth in its upper portion. The microretentive ridges in the lower portion of the wall assist in the positive retention of the material used to fill the cavity, while the generally smooth upper portion prevents microfracturing of the tooth enamel and/or filling material resulting from mastication pressure. Each of the flutes includes a cutting edge having a plurality of recesses in its lower portion and a nonrecessed area in its upper portion. The recesses produce the ridges in the cavity wall. The flute design allows the simultaneous smooth surfacing of the upper portion of the wall and the production of the ridges in the lower portion of the wall. The ratios of the recessed and nonrecessed areas of the cutting edges of the flutes may vary as desired. Each of the flutes may be provided with a radiused edge joining the cavity wall cutting edge with a cutting edge for the bottom surface of the cavity. This radiused edge produces a cavity preparation having a smooth transition rom the cavity wall to the cavity floor. This relieves the internal stress points and sharp line angles in the cavity preparation and reduces the possibility of future tooth fracture at the juncture of the cavity wall and cavity floor.

27 Claims, 12 Drawing Figures

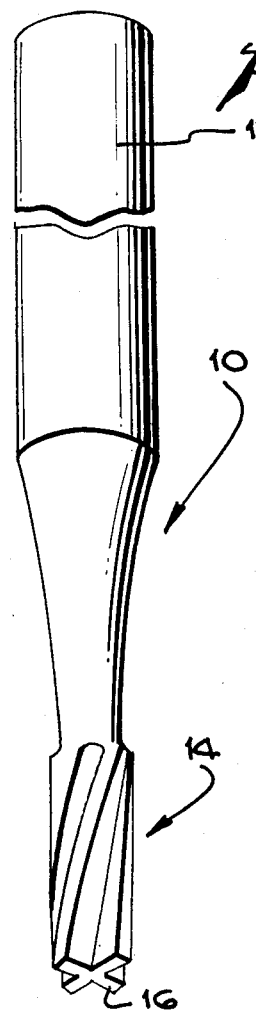
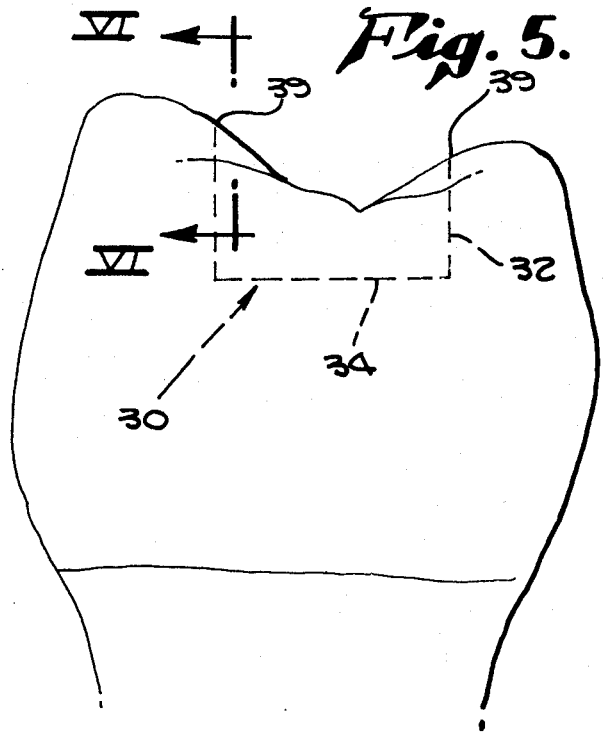
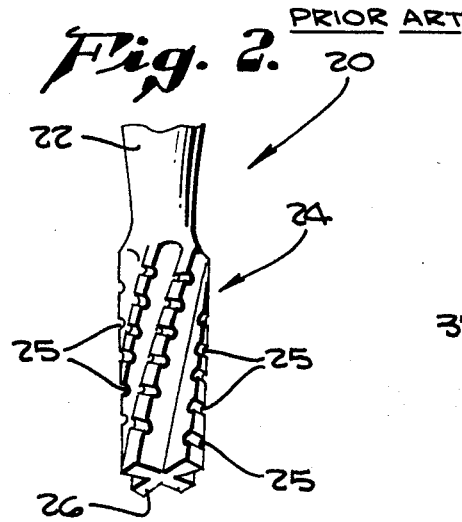
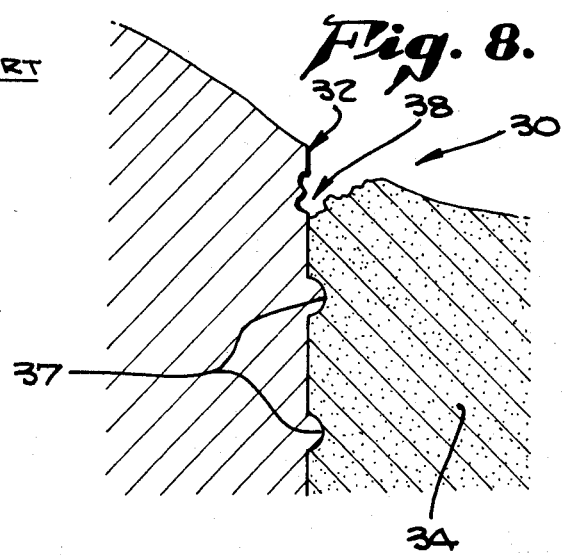

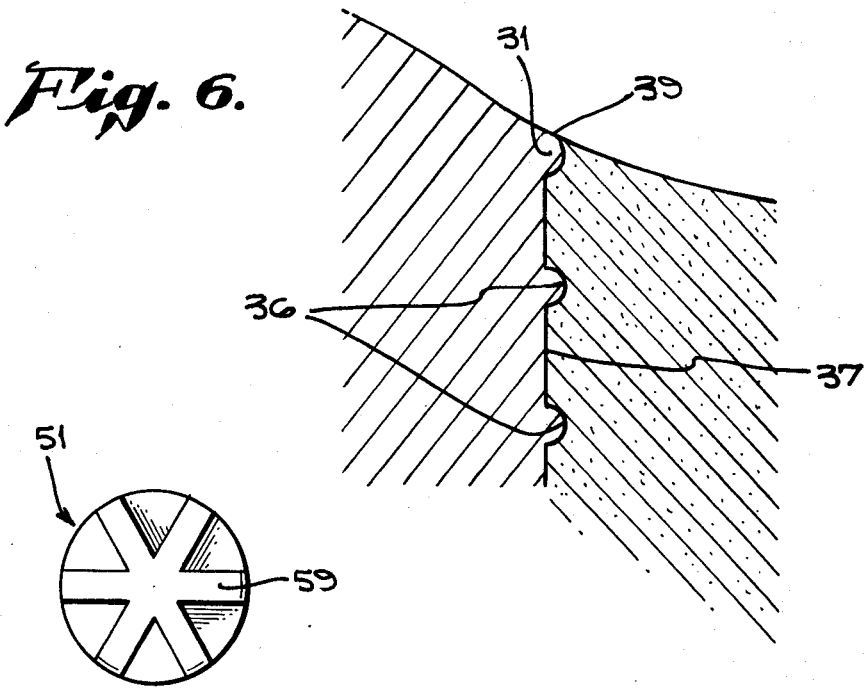
Fig. 6.
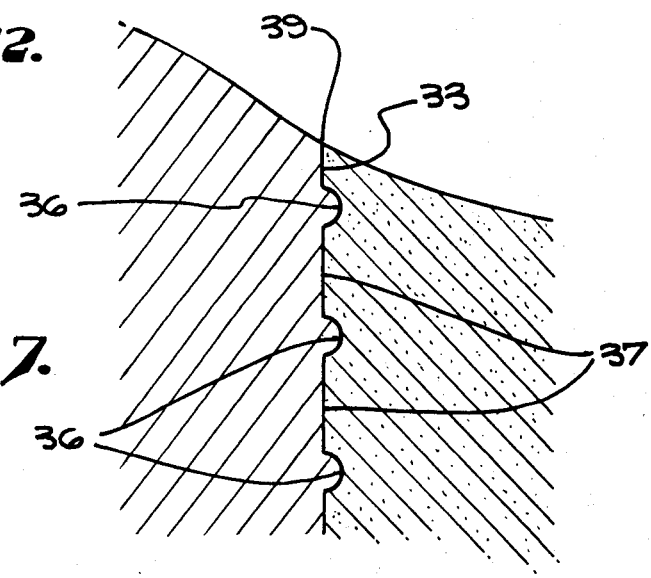
Fig. 12.
Fig. 7.

DENTAL TOOTH BUR

FIELD OF THE INVENTION

The present invention relates, in general, to dental equipment and, in particular, to dental tooth burs.

BACKGROUND OF THE INVENTION

Little improvement in the dental tooth bur art has been made in the past 90 years. The tooth burs currently in use reflect only slight modifications to those described in U.S. Pat. No. 418,108 (Browne), dated 1889. Browne describes two versions of a dental tooth bur, one having straight flutes, and one having crosscut flutes. Both types of flutes have distinct limitations.

When a tooth cavity is prepared for filling with a dental bur having smooth flutes (ones without crossgrooves), a large amount of heat is generated, the enamel is not cut efficiently, and the cavity walls do not have any interiorly-projecting microretentive ridges to assist in the retention of the filling material. However, a cavity prepared with a noncrosscut bur does have the advantage of a completely straight wall, which provides the greatest shear strength against fracture due to mastication pressure because the enamel is cut completely parallel to the origin of the enamel rod crystals and as near perpendicular to the surface of the tooth as possible. This shear strength is especially important at the upper edge of the wall because of the exposed margin or interface between the filling material and the tooth enamel. It is this margin area which is especially susceptable to microfracturing.

By contrast, when a tooth cavity is prepared for filling with a bur having crossgrooved flutes, the cutting can be done more efficiently and with less heat. The cutting also produces generally annular microretentive ridges to assist in the retention of the filling material. However, a cavity prepared with a crossgrooved bur has the serious deficiency of having the microretentive ridges near the upper edge of the cavity wall. As a result, normal mastication pressure can eventually cause microfracturing of the tooth enamel and the filling material at the margin of the enamel and the filling material. This microfracturing produces small voids in the margin area. These voids contribute to corrosion of the filling material, plaque retention, percolation of fluids within the filling, enamel decalcification, and other forms of tooth deterioration.

The problem is presented, therefore, of how to obtain the beneficial aspects of a cavity prepared with a crossgrooved bur and yet minimizing microfracturing, as would be possible with a bur without crossgrooves. Obviously, a dentist could first cut and remove the decayed portion of the tooth with a crossgrooved fluted bur and then change to a smooth (or noncrossgrooved) fluted bur to redefine the upper portion of the cavity. This process would allow the efficient, low-heat cutting of the enamel to prepare the tooth and would produce microretentive ridges in the lower portion of the prepared cavity walls, while leaving the margin areas smooth and honed to allow the enamel and filling material to have maximum strength. As this method would present a complication and an addition to the normal procedures followed for preparing cavities for filling, it is not a completely satisfactory solution to the problem.

A more practical solution would be to provide a tooth bur capable of both the honing of a cavity wall and the production of ridges in that wall. However, in the approximately 90 years since the issuing of the Browne patent, no such improvement has been achieved.

Another problem with the tooth burs found in the prior art is that such burs generally have right-angled edges between the portions of the bur which cut the cavity wall, and the portions of the bur which cut the cavity floor. Such burs produce a cavity preparation having a cavity wall which intersects the cavity floor at approximately a right angle, thereby producing sharp internal line angles in the tooth enamel and/or dentin at this point. These line angles are internal stress points for possible fracturing of the restored tooth. If the sharp internal line angles of the cavity preparation could be eliminated, the completed preparation would be much stronger.

Accordingly, it is the principal object of the present invention to provide a dental bur capable of simultaneously smoothly honing the upper portion of a cavity wall and creating internally-projecting microretentive ridges in the lower portion of the cavity wall.

It is a further object of this invention to simultaneously hone the upper portion of a cavity wall and create microretentive ridges in the lower portion of the cavity wall with dental burs of different shapes.

It is another object of the present invention to prevent microfracturing at the upper portions of a tooth cavity wall.

Yet another object of the present invention is to prepare a tooth cavity wall quickly and efficiently with a minimum of heat generation.

Another object of the present invention is to provide a sufficient number of generally annular microretentive ridges in the lower portion of a cavity wall to assist in the retention of the material used to fill the cavity without weakening the upper portion of the cavity wall, thereby eliminating or minimizing the possibility of microfracturing of the tooth and/or filling material.

A further object of the present invention is to reduce the sharp internal line angles in a cavity preparation to strengthen the finished restoration of the tooth by reducing the possibility of tooth fracture at the junction of the cavity wall and floor.

SUMMARY OF THE INVENTION

The present invention, in a broad aspect, provides a dental tooth bur capable of producing a cavity wall having a plurality of ridges in the lower portion of the wall and a nonridge surface in the upper portion of the wall. The nonridged surface provides maximum shear strength for the upper portion of the wall to prevent microfracture of the tooth enamel and/or filling material in the margin area. The ridged surface provides appropriate microretention to prevent the cavity filling material from leaving the cavity.

In accordance with one feature of the invention, the nonridged surface can be a generally smooth and honed surface.

In accordance with a yet another feature of the invention, the ridged and nonridged portions of the cavity walls can vary in proportion. For example, the ridged surface could comprise the lower one-third of the wall, and the nonridged (or smooth) surface could comprise the upper two-thirds of the wall. The ridged surface could also comprise the lower one-half of the wall, with the nonridged surface comprising the upper one-half of the wall. Other ratios could also be utilized.

In accordance with a further feature of the invention, the ridges in the lower portion of the cavity wall can be generally annular or helical, or may be combinations thereof.

In accordance with another feature of the invention, the tooth bur producing the cavity wall includes a plurality of flutes at one end of a shank, with the lower portion of the flutes having cutting edges with a plurality of generally arcuate recesses or grooves to produce the ridged surface on the lower portion of the cavity wall, and with the cutting edge in the upper portion of the flutes beng nonrecessed or generally smooth to produce the honed surface in the upper portion of the wall.

In accordance with another feature of the invention, the overall shape of the fluted cutting end of the bur may be straight, tapered, conical, round, oval or any combination thereof to produce a cavity wall with the features described hereinabove. Also, the flutes may be angularly disposed relative to the shank axis to produce a spiraling of the flutes.

In accordance with another feature of the invention, the flute may contain appropriate cutting edges to produce a smooth bottom portion for the cavity. The cutting edges producing the smooth bottom surface may be joined to the wall cutting edges by a slightly rounded or radiused edge on each of the flutes. This slightly-curved or radiused edge produces a smooth transition from the cavity wall to the bottom surface of the cavity to relieve the internal stress points of the cavity preparation and thus to resist the fracturing of the restored tooth at the junction of these surfaces.

Other objects, features, and advantages of the present invention will become apparent from a consideration of the following detailed description and from the accompanying drawings.

BRIEF DESCRIPTION OF THE DRAWINGS

FIG. 1 shows a prior art tooth bur having straight flutes;

FIG. 2 shows a prior art tooth bur having crossgrooved flutes;

FIG. 5 shows a fragmentary view of the tooth cavity shown in FIG. 4, after said cavity has been filled;

FIG. 6 shows a detail view of FIG. 5, taken through the plane VI—VI;

FIG. 7 shows an alternate view of FIG. 5, in a view similar to that of FIG. 6;

FIG. 8 shows a detailed view of the microfracturing possible with the cavity shown in FIG. 5, in a view similar to that of FIG. 6;

FIG. 12 shows an end view of the tooth bur of FIG. 9 taken through the plane XII—XII.

DETAILED DESCRIPTION

Figure 3:
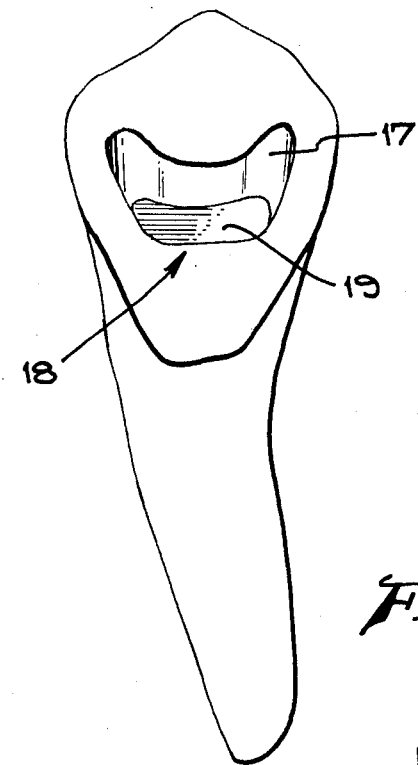
FIG. 3 shows a tooth cavity prepared with the prior art tooth bur shown in FIG. 1.
Figure 4:
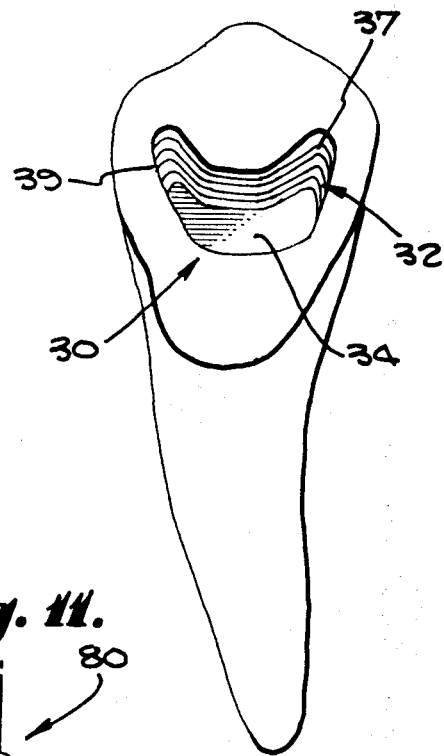
FIG. 4 shows a tooth cavity prepared with the prior art tooth bur shown in FIG. 2.

Referring more particularly to the drawings, FIGS. 1 and 2 show prior art versions 10 and 20 of tooth burs having straight and crossgrooved flutes, respectively. FIGS. 3 and 4 show perspective views of tooth cavities prepared with the tooth burs shown in FIGS. 1 and 2, respectively. The tooth burs shown in FIGS. 1 and 2 are typical of the tooth burs currently used by the dental profession. As previously mentioned, the designs of the tooth burs shown in FIGS. 1 and 2 are practically identical to the those disclosed in U.S. Pat. No. 481,108 (Browne), granted in 1889. Little improvement has been made in the tooth bur art since Browne.

Referring to FIG. 1, the prior art bur 10 shown therein generally comprises a shank portion 12 having a plurality of flutes 14 at one end. These flutes 14 have generally straight cutting edges. Additionally, each of the flutes 14 has an additional cutting edge 16 at its end to remove material from the bottom of the cavity. The cavity prepared with the dental bur of FIG. 1 is shown in FIG. 3. As can be seen, the cavity, generally denoted 18, has a generally smooth cavity wall 17 and a relatively flat bottom surface 19 junctioning at approximately right angles. As described, the use of the straight flute bur 10 to prepare the cavity 18 has several disadvantages. First, the tooth enamel is not cut efficiently. Second, great amounts of heat are generated. Third, there are no microretentive ridges in the cavity to retain the filling material. Fourth, the perpendicular junction of the cavity wall 17 and the cavity floor 19 makes the tooth very susceptible to fracture at the corner formed at the junction. Fifth, the straight flute burs "chatter" vigorously when used at high speed, which not only produces trauma to the tooth, but also damages the delicate bearings in the dental handpiece or drill. The beneficial effect of the straight-flute bur 10, however, is that the bur 10 leaves the enamel honed parallel to the origin of the enamel rod crystals and perpendicular to the surface of the tooth. This provides maximum shear strength for the cavity wall 17 and resists microfracturing of the upper edge of the wall 17 caused by mastication pressure.

Referring to FIG. 2, the prior art bur 20 shown therein includes a shank 22 having a plurality of flutes 24 crossgrooved by the inclusion of a plurality of recesses 25. These recesses 25 are typically disposed on the flutes to produce generally helical ridges in a cavity preparation, although some prior art burs have produced annular ridges. The flutes 24 are also each provided with a lower cutting edge 26 to prepare the bottom surface of the cavity. FIGS. 4–7 show the cavity 30 prepared with the prior art tooth bur shown in FIG. 2. As shown in FIG. 4, the cavity 30 includes a cavity wall 32 having a plurality of microretentive ridges 37 parallel to the bottom surface of the cavity 34. As described, the use of the crossgrooved bur 20 to prepare the cavity 30 allows the cavity walls to be formed with a minimum of heat, and with a much more efficient cutting action than is possible with the smooth bur. Also, the microretentive ridges in the cavity wall 32 assist in the retention of the cavity filling material.

FIGS. 5 through 8, however, show the serious deficiency in the cavity wall 32 resulting from the use of the crossgrooved bur 20. As shown in FIGS. 6 and 7, the ridges 37 left in the cavity wall will either produce an unsupported cornice 31 in the enamel (FIG. 6) or an unsupported cornice 33 in the filling material (FIG. 7) depending upon the relative location of the bur edge recesses 25 and the margin 39 of the cavity wall 32 and the filling material 35. Due to the changing contour of the tooth, the tooth will usually have both unsupported enamel cornices 31 and unsupported filing material cornices 33 within the same cavity preparation. Moreover, when the bur recesses 25 are disposed on the flutes 24 to produce generally helical ridges 37 in a cavity wall 32, an unsupported cornice will occur at the upper termination of each ridge 37. These cornices are very fragile and susceptible to the microfracturing shown in FIG. 8.

As shown in FIG. 8, the microfracturing of the enamel and/or filling material cornices occurs near the upper edge of the cavity, and most specifically at the margin 39. Such a fracturing is generally indicated at 38. This fracturing occurs as a result of mastication pressure and results in the destruction of one or more of the enamel and/or filling material cornices at the margin 39 of the cavity wall 32 and the filling material 35. This fracture leaves a void at the margin 39 in either the enamel, or in the filling material or in both. This void accelerates corrosion and deterioration of the filling material, retention of plaque, percolation of fluids into the cavity area, enamel decalcification, and other forms of tooth decay and deterioration.

The present invention is directed toward the elimination of the microfracturing of the enamel and/or filling material cornices in the margin or interface area between the tooth enamel and the filling material. (As discussed hereinafter, the present invention is also directed toward the elimination of the sharp line angles in the tooth enamel or dentin at the juncture of the cavity walls and cavity floor). To eliminate the microfracturing, the present invention provides a tooth bur which simultaneously produces (in the final stages of the cavity preparation) a ridged lower cavity wall and a nonridged upper cavity wall. In the best mode contemplated for the invention, the ridges in the lower cavity wall are generally annular, and the upper cavity wall is generally smooth and honed. Such a bur thus combines the beneficial features of the straight fluted burr 10 shown in FIG. 1, with those of the crossgrooved fluted bur shown in FIG. 2. Additionally, the production of annular ridges in the lower portion of the tooth is a marked improvement over the generally helical ridges produced by the crossgrooved burs 20 currently manufactured. As discussed, these helical ridges generally exacerbate the microfracturing at the margin 39.

Figure 9:
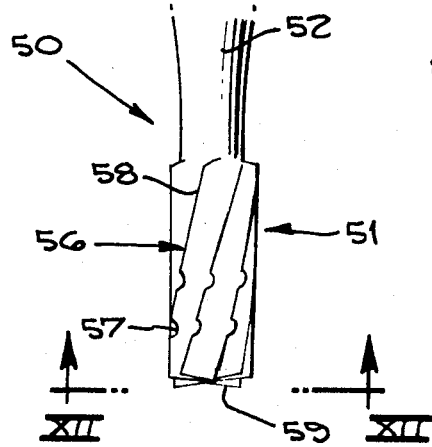
FIG. 9 shows a perspective view of one embodiment of a tooth bur according to the present invention.
Figure 10:
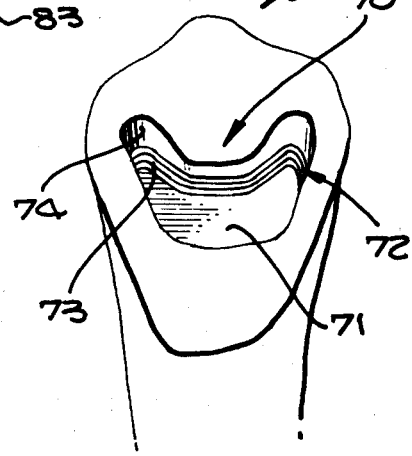
FIG. 10 shows a cavity prepared with the tooth bur shown in FIG. 9.

FIG. 9 shows a perspective view of one embodiment 50 of a novel tooth bur according to the present invention. FIG. 12 shows an end view of the tooth bur of FIG. 9. As shown therein, the bur 50 includes a shank 52 having at one end a plurality of flutes 51. Each of the flutes includes a longitudinal cutting edge 56 having one or more generally arcuate recesses or grooves 57 in the lower portion of the edge and a generally nonrecessed or straight portion 58 in the upper part of the edge. In this manner, the flutes produce microretentive ridges in the lower portion of a cavity wall while simultaneously producing smooth and honed surface in the upper portion of the cavity wall. Such a cavity 70 is shown in FIG. 10. The cavity 70 includes a cavity wall 72 having a plurality of generally annular and interiorly-projecting ridges 73 in the lower portion of the cavity wall 72, with a generally smooth and honed surface 74 in the upper portion of the wall 72. The bur 50 also includes a cutting edge 59 at the end of each of the flutes 51 to produce a smooth bottom surface 71 for the cavity 70. It should be noted that while, in the best mode contemplated for the invention, the recesses 57 are disposed on the cutting edges 56 of the flutes to produce ridges in the lower portion of the cavity wall which are generally annular, the recesses 57 could also be disposed on the cutting edge 56 to produce ridges which are generally helical.

Regarding the shape of the recesses 57, while they have been shown in FIGS. 9 and 10 as generally arcuate or semicircular, other shapes could also be employed. For example, the recesses 57 could be V-shaped or generally rectangular. The particular shape employed for the recesses 57 will depend upon the particular application in which the bur is used.

The ratio of the crossgrooved (by way of the recesses 57) and the noncrossgrooved portions of the cutting edge 56 may vary depending on the desired amount of microretentive ridges in the cavity wall. For example, the crossgrooved portion could comprise the lower one-third of the edge 56 with the noncrossgrooved portion 58 comprising the upper two-thirds of the edge 56. The crossgrooved portion could also comprise the lower one-half of the edge 56, with the noncrossgrooved portion 58 comprising the upper one-half of the edge. The crossgrooved portion could also comprise the lower two-thirds of the edge, with the noncrossgrooved portion 58 comprising the upper one-third. Other ratios may also be employed, so long as the crossgrooved portion 57 is below the noncrossgrooved portion 58. The particular ratio chosen will determine the quantity of microretentive ridges in the lower portion of the cavity wall. The optimum number of microretentive ridges will depend on such factors as the particular filling material used, the strength of the tooth, and the professional opinion of the practitioner.

The novel tooth bur 50 of the present invention allows the cavity 70 prepared therewith to be created very efficiently and without heat, chatter, tooth trauma, drill bearing damage, or loading of the bur with debris, because the bulk of the initial removal of decayed tooth material from the cavity area is done with the lower (crossgrooved) portion of the bur 50 as the bur 50 penetrates downwardly into the tooth. As the cavity 70 reaches its final stages of preparation, the noncrossgrooved upper portions 58 of the flute cutting edges 56 are in contact with the upper portion of the cavity wall 72, while the crossgrooved lower portions of the flute cutting edge 56 are in contact with the lower portion of the cavity wall 72. Accordingly, the smooth and honed surface 74 is produced in the upper portion of the cavity wall 72 simultaneous with the generally annular ridges 73 in the lower portion of the cavity wall 72. The ability to simultaneously produce a smooth and honed upper cavity wall with a ridged lower cavity wall will allow the shaping of the cavity wall much more rapidly than with the burs of the prior art. The final cross sectional shape of the cavity produced with the novel tooth bur of the present invention is rectangular with a smooth bottom surface joining a cavity wall that has a ridged lower portion 73 and a generally smooth upper portion 74.

The novel tooth bur 50 can be made utilizing standard manufacturing techniques and material, such as high-carbon or carbide steel. Furthermore, various modifications can be made to the shape of the bur 50 to further enhance its novel properties. For example, the fluted end 51 of the bur 50 may be straight, round, oval, tapered (toward the end of the bur 50) or conical (tapered toward the bur shaft 52). Furthermore, any combination of these shapes may also be employed. For example, the fluted end 51 could have a straight portion adjacent a conical portion; a tapered portion merging into a straight portion, which merges into an oval portion; or a tapered portion and a conical portion placed back-to-back. Other modifications may also easily be envisioned. Also, and as shown in FIG. 9, the flutes 51 may be angularly disposed relative to the longitudinal axis of the shank 52, thereby producing a spiralling of the flutes 51 relative to the shank axis. Furthermore, while the flutes 51 have been shown in FIG. 9 as having cutting edges 56 which are relatively straight, curved cutting edges could also be utilized to achieve the beneficial results of the present invention. It should be noted that while dental burs currently manufactured are designed to rotate in a clockwise direction, the flutes 51 may be arranged on the bur 50 for counterclockwise or clockwise rotation.

It should also be noted that one modification contemplated within the scope of the present invention is the use of raised lobes on the flute cutting edges 56 in place of the generally arcuate or semicircular recesses. This arrangement would produce ridges on the bur 50 which would cut grooves into the lower portion of the cavity wall, as opposed to the opposite arrangement as shown in FIG. 9.

Figure 11:
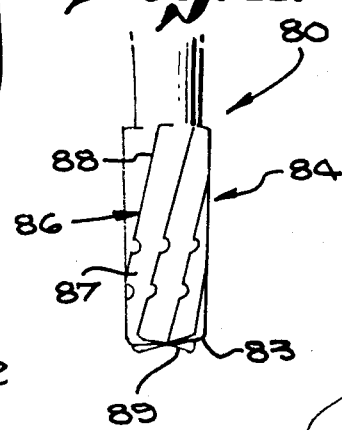
FIG. 11 shows a fragmented view of another embodiment of a tooth bur according to the present invention.

One important alternative embodiment 80 of the present invention is shown in FIG. 11. This embodiment is generally similar to the embodiment 50 shown in FIG. 9, insofar as it includes flutes 84 with a wall cutting edge 86 which is crossgrooved in its lower portion 87 with a plurality of generally arcuate recesses and smooth in its upper portion 88, and with a bottom cutting edge 89. However, the tooth bur 80 incorporates a slightly curved or radiused edge 83 for each of the flutes 84 to interconnect the longitudinal cutting edge 86 with the lower or transverse cutting edge 89. This edge or corner 83 produces a smooth transition from the cavity wall 72 to the cavity floor 71 to prevent sharp internal line angles in the cavity preparation 70 which contribute to possible fracture of the restored tooth at the junction of the cavity wall 72 and the cavity floor 71. The sharp internal line angles result from using burs having approximately right-angled edges between the longitudinal and transverse cutting edges, such as shown in the prior art bur 10 of FIG. 1. Such burs produce the cavity preparation 18 shown in FIG. 3, having a cavity wall 17 which junctures the cavity floor 19 at approximately a right angle, thereby producing sharp internal line angles in the cavity preparation, which become internal stress points for the preparation and restored tooth. The use of the slightly-curved or radiused edges 83 lowers the stress point line angles and thus strengthens the preparation. Furthermore, the curved edges 83 prevent excess heat and pulp nicks during the preparation of the cavity 70.

As can be seen from the foregoing, the two embodiments 50 and 80 of the novel tooth bur according to the present invention represent major improvements in the state of the dental bur art, which has not seen significant progression in the last 90 years. The use of such dental burs will result in cavity preparations which will be both stronger and longer lasting and which will not require special drilling techniques.

In the foregoing description of the present invention, two alternate embodiments of the invention have been disclosed. It is to be understood that many other mechanical and design variations are within the scope of the present invention. As mentioned, the cutting edges 56 and 86 of flutes 51 and 84 could utilize different ratios for crossgrooved and noncrossgrooved portions. Also, the bur could be provided with alternating crossgrooved and noncrossgrooved portions for each of the flutes 51 and 84, so long as the upper portions of the flutes 51 and 84 are not grooved. Finally, and as mentioned hereinabove, while the generally annular ridges produced by the burs 50 and 80 is achieved with the use of recesses on the tooth burs, raised teeth could be substituted for the recesses to produce microretentive grooves in at least one lower portion of the cavity wall. Accordingly, the invention is not limited to the particular arrangement which has been illustrated and described in detail herein.

What is claimed is:

1. A dental tooth bur for preparing a tooth cavity for filling comprising:
    cutting means for producing a wall for said tooth cavity having a nonridged surface a first region and having a continuously crossridged surface in a second region vertically beneath said first region, whereby said nonridged surface provides maximum shear strength for said wall and said crossridged surface assists in the retaining of the material with which said cavity is filled.
2. A dental tooth bur as defined in claim 1, wherein:
    said cutting means produces said nonridged surface in an upper region of said wall, and produces said crossridged surface in a lower region of said wall, whereby:
    (i) said nonridged surface prevents microfracturing of the tooth enamel and of said filling material at the upper edge of said wall caused by mastication pressure, and
    (ii) said crossridged surface provides microretentive ridges to assist in the retention of said filling material.
3. A dental tooth bur as defined in claim 2, wherein:
    said nonridged surface comprises a generally smooth and honed surface;
    said crossridged surface comprises a plurality of interiorly projecting ridges; and
    said means produces said smooth surface in the upper two-thirds of said cavity wall and produces said crossridged surface in the lower one-third of said cavity wall.
4. A dental tooth bur as defined in claim 2, wherein:
    said nonridged surface comprises a generally smooth and honed surface;
    said crossridged surface comprises a plurality of interiorly projecting ridges; and
    said means produces said smooth surface in the upper one-half of said cavity wall and produces said crossridged surface in the lower one-half of said cavity wall.
5. A dental tooth bur as defined in claim 2, wherein:
    said nonridged surface comprises a generally smooth and honed surface;
    said crossridged surface comprises a plurality of interiorly projecting ridges; and
    said means produces said smooth surface in the upper one-third of said cavity wall and produces said crossridged surface in the lower two-thirds of said cavity wall.
6. A dental tooth bur as defined in claim 2, wherein said ridged surface comprises a plurality of interiorly projecting annular ridges.

7. A dental tooth bur as defined in claim 2, wherein said ridged surface comprises a plurality of interiorly projecting helical ridges.

8. A dental tooth bur as defined in claim 2, wherein said ridged surface comprises a plurality of interiorly projecting ridges generally semicircular in cross section.

9. A dental tooth bur as defined in claim 2, wherein said ridged surface comprises a plurality of interiorly projecting ridges generally triangular in cross section.

10. A dental tooth bur as defined in claim 2, wherein said ridged surface comprises a plurality of interiorly projecting ridges generally square in cross section.

11. A dental tooth bur as defined in claim 1, wherein said cutting means comprises:
   a shank portion;
   a plurality of cavity wall cutting edges disposed longitudinally at one end of said shank, each of said edges having a first portion containing a plurality of recesses to produce said crossridged surface, and having a second portion above said first portion that is substantially straight to produce said nonridged surface.

12. A dental tooth bur as defined in claim 11, wherein:
   said first portion comprises the lower one-third of each of said edges; and
   said second portion comprises the upper two-thirds of each of said edges.

13. A dental tooth bur as defined in claim 11, wherein:
   said first portion comprises the lower one-half of each of said edges; and
   said second portion comprises the upper one-half of each of said edges.

14. A dental tooth bur as defined in claim 11, wherein:
   said first portion comprises the lower two-thirds of each of said edges; and
   said second portion comprises the upper one-third of each of said edges.

15. A tooth bur as defined in claim 11, wherein:
   said edges are shaped to produce a cutting end for said shank that is tapered.

16. A tooth bur as defined in claim 11, wherein:
   said edges are shaped to produce a cutting end for said shaft that is conical.

17. A tooth bur as defined in claim 11, wherein:
   said edges are shaped to produce a cutting end for said shank that is rounded.

18. A dental tooth bur as defined in claim 11, wherein:
   said wall cutting edges are disposed at said shank end at an angle relative to said longitudinal axis of said shank, whereby said plurality of wall cutting edges axially spiral along said axis.

19. A tooth bur as defined in claim 11, wherein said tooth bur further comprises:
   means for producing a generally flat bottom surface for said cavity; and
   means for producing a slightly curved corner between said cavity wall and said bottom surface, thereby producing a smooth transition between said wall and said bottom surface to resist tooth fracture at the juncture thereof caused by mastication pressure.

20. A tooth bur as defined in claim 19, wherein:
   said means for producing a generally flat bottom surface comprises a plurality of bottom surface cutting edges disposed perpendicularly to the longitudinal axis of said shank at the end of said wall cutting edges; and
   said means for producing a curved corner comprises a plurality of radiused cutting edges joining said wall cutting edges with said bottom cutting edges.

21. A dental bur, comprising:
   a shank;
   a plurality of flutes longitudinally disposed at one end of said shank, said flutes each comprising a generally straight cutting edge having a first portion with a plurality of recesses and having a second portion above said first portion and having no recesses, whereby said bur prepares a tooth cavity for filling having a vertical cavity wall which is unridged in one region and crossridged in a region beneath said unridged region, with said unridged region preventing microfracturing of the tooth enamel and of the material used to fill said cavity, and with said crossridged region assisting in the retaining of said cavity filling material.

22. A dental bur as defined in claim 21, wherein:
   said unridged surface comprises substantially smooth surface;
   said crossridged surface comprises a plurality of interiorly projecting ridges; and
   said first portion of said edge is vertically beneath said second portion of said edge, whereby:
   (i) said second portion of said edge produces a smoothly honed region in the upper region of said cavity wall to provide said wall and said filling material adjacent said wall with maximum strength against mastication pressure, and
   (ii) said first portion produces a plurality of microretentive ridges in the lower region of said cavity wall to assist in the retention of said filling material within said cavity.

23. A dental bur as defined in claim 22, wherein:
   each of said flutes is axially tapered along the longitudinal axis of said shank.

24. A tooth bur as defined in claim 23, wherein:
   said edges taper in a direction away from said shank, thereby producing a conical cutting end for said shank.

25. A tooth bur as defined in claim 23, wherein:
   said edges taper in a direction toward said shank, thereby producing an inversely-tapered cutting end for said shank.

26. A tooth bur as defined in claim 22, wherein:
   said flutes are angularly disposed at said shank end relative to the longitudinal axis of said shank, whereby said flutes axially spiral along said axis.

27. A tooth bur as defined in claim 22, wherein said bur further comprises:
   a bottom cutting edge disposed at the end of each of said flutes in perpendicular relation to the axis of said shank to producing a generally flat and smooth bottom surface in said cavity; and
   a radiused edge on each of said flutes joining said bottom cutting edge and said wall cutting edges to produce a smooth transition between said cavity wall and said cavity bottom surface to prevent fracturing between said wall and said bottom surface produced by mastication pressure.

* * * * *